United States Patent
Specht

(10) Patent No.: US 6,446,294 B1
(45) Date of Patent: Sep. 10, 2002

(54) ELECTRIC TOOTHBRUSH

(75) Inventor: Paul Bernhardt Specht, Wilmette, IL (US)

(73) Assignee: Unilever Home & Personal Care USA, division of Conopco, Inc., Greenwich, CT (US)

(*) Notice: Subject to any disclaimer, the term of this patent is extended or adjusted under 35 U.S.C. 154(b) by 0 days.

(21) Appl. No.: 09/457,643

(22) Filed: Dec. 9, 1999

(51) Int. Cl.[7] ............................................... A46B 13/02
(52) U.S. Cl. ........................... 15/22.1; 15/22.2; 74/23; 433/118; 433/122; 433/131
(58) Field of Search .................................. 15/22.1, 22.2, 15/20, 23; 433/118, 122, 130, 131; 74/23

(56) References Cited

U.S. PATENT DOCUMENTS

| | | | |
|---|---|---|---|
| 3,435,477 A | 4/1969 | Moyer | 15/22.1 |
| 3,538,530 A | 11/1970 | Stemme | 15/22.1 |
| 3,577,579 A | 5/1971 | Duve et al. | 15/22.1 |
| 3,588,936 A | 6/1971 | Duve | 15/22.1 |
| 3,676,218 A | 7/1972 | Sawyer | 15/22.2 |
| 4,276,672 A | 7/1981 | Teague, Jr. et al. | 15/22.1 |
| 4,756,202 A | 7/1988 | Kawamoto | 15/22.1 |
| 4,989,287 A | 2/1991 | Scherer | 15/22.1 |
| 5,077,855 A | 1/1992 | Ambasz | 15/22.1 |
| 5,173,983 A | 12/1992 | Le | 15/28 |
| 5,177,826 A | 1/1993 | Vrignaud et al. | 15/22.1 |
| 5,467,494 A | 11/1995 | Muller et al. | 15/22.1 |
| 5,577,285 A | 11/1996 | Drossler | 15/22.1 |
| 5,617,603 A | 4/1997 | Mei | 15/22.1 |
| 5,822,821 A | 10/1998 | Sham | 15/22.1 |
| 5,842,245 A | 12/1998 | Pai | 15/22.1 |

FOREIGN PATENT DOCUMENTS

| | | | |
|---|---|---|---|
| CH | 435553 | * 10/1967 | 15/22.1 |
| DE | 3218596 | * 11/1983 | 15/22.1 |
| DE | 3244262 | * 5/1984 | 15/22.1 |
| FR | 1 250 455 | 10/1959 | |
| JP | 52-4358 | * 1/1977 | 15/22.1 |
| WO | 98/23223 | 6/1998 | |

* cited by examiner

*Primary Examiner*—Gary K. Graham
(74) *Attorney, Agent, or Firm*—Milton L. Honig

(57) ABSTRACT

An electric toothbrush is provided which includes an elongate body having an interior cavity, a power source mounted within the cavity, an elongate drive shaft driven rotatably by the power source, a camwheel mounted on the drive shaft, a yoke with projecting arms which confine travel of the camwheel, a crankshaft section driven by the drive shaft, an output shaft axially aligned to the drive shaft, and a collar with a guide track eccentrically coupling the crankshaft section to the output shaft thereby imparting both lateral and rotary reciprocating motion to the output shaft. A brushhead mounted on the front end of the elongate body accepts the motion from the output shaft. The mechanical drive system is fully enclosed within the housing of the elongate body. Brushheads are replaceably mountable outside the cavity on the front end.

6 Claims, 3 Drawing Sheets

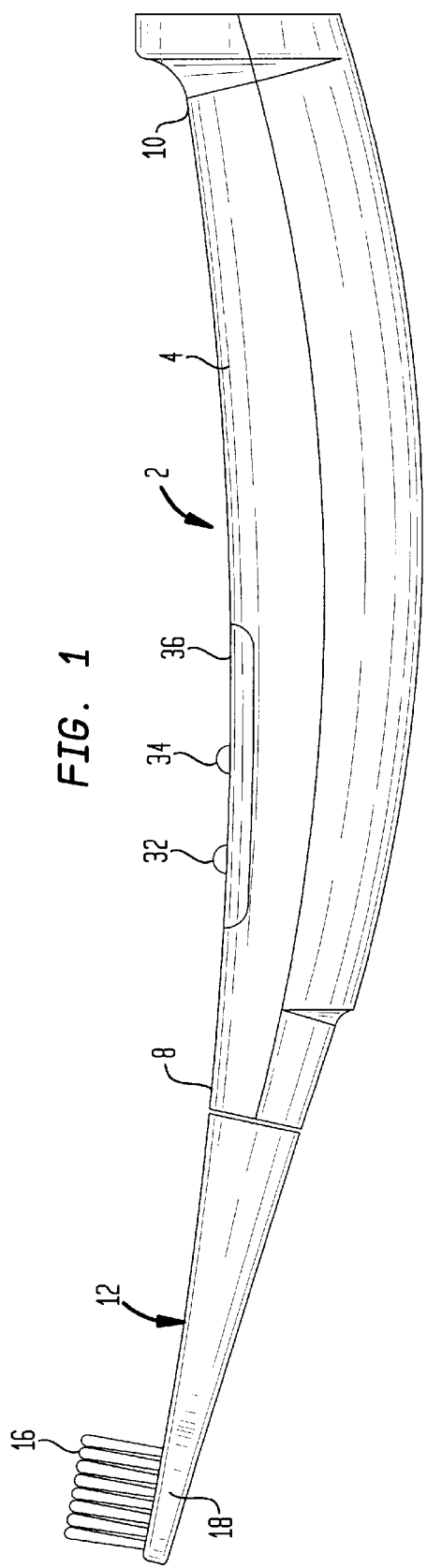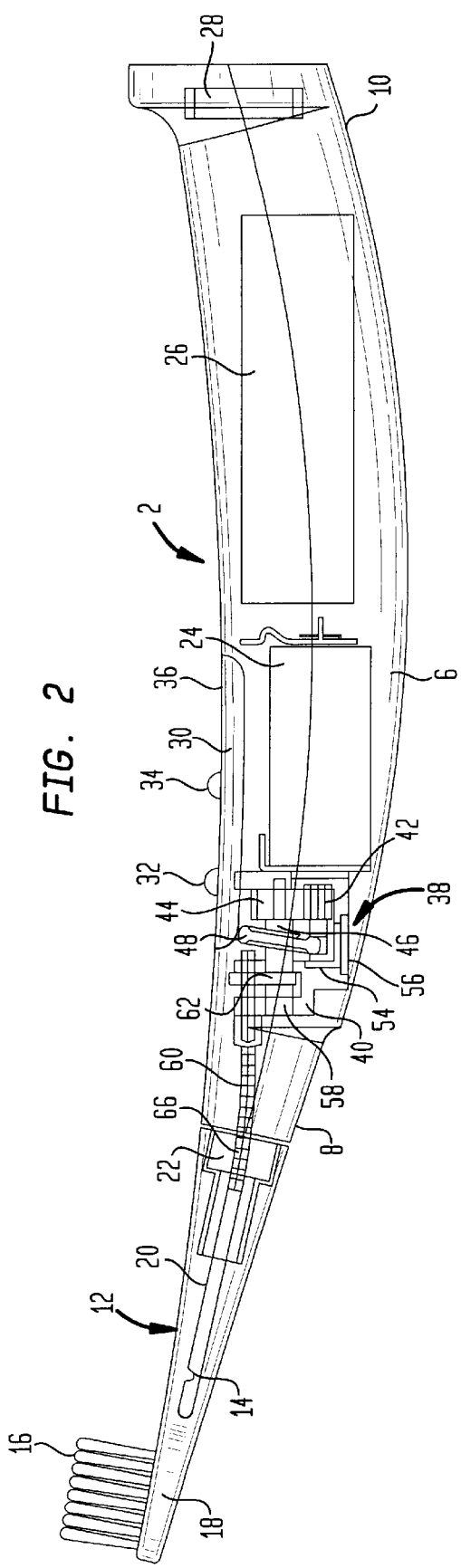

ELECTRIC TOOTHBRUSH

BACKGROUND OF THE INVENTION

1. Field of the Invention

The invention concerns an electric toothbrush which operates a brushhead with three dimensional stroke movement.

2. The Related Art

Electric toothbrushes have been in development for over sixty years. The earliest type were relatively simple, electromechanical versions of manual toothbrushes with limited back-and-forth movement. More recent developments have featured enhanced performance batteries and high efficiency miniaturized electric motors. Today battery powdered electric toothbrushes figure prominently in the general product classification.

Yet with these drive train improvements, the basic electromechanical arrangement differs little from the earliest devices marketed. Essentially, the typical product consists of a battery, either rechargeable or replaceable, adjacent end to end to a small high speed electric motor. A drive shaft operated by the motor may in turn either be coupled to a mechanical drive train with reduction gears or crank arms or may be coupled with simple direct drive.

Most mechanical designs involve an oscillating fixed bristle array brush operating with a narrow back and forth angular range of rotary motion. Travel is essentially in a two dimensional plane. Various types of mechanical devices such as gears with levers, in combination or separately, deliver the rotary motion. In some instances, the brushhead may feature individually rotatable brush bundles driven by gearing alone. A third category of electric brush incorporates ultrasonic technology, either alone or in combination with an oscillating brush.

Among the considerable volume of literature is U.S. Pat. No. 5,577,285 (Drossler) which describes an electric toothbrush in which a rotary shaft translates to a bristle supporting structure an alternating or a rotary motion. U.S. Pat. No. 5,467,494 (Muller et al.) describes a mechanism with a pair of mutually pivotable parts, the first serving as a handle and the second a brushhead. A spring arranged between the parts snaps when a given pressure threshold is exceeded and resumes its original position when the pressure is decreased. Angular rotation is imparted by the spring action. U.S. Pat. No. 4,276,672 (Teague, Jr. et al.) reports a water powered nutating system effectuating a rotary motion which in turn converts to an orbital motion in the brush working element. U.S. Pat. No. 3,538,530 (Stemme) provides a motor-driven toothbrush based on a guide arrangement with cam faces with an outline resembling a figure eight. The guide shifts that portion of a brush stem extending into the housing. Thereby the entire brush operates along a path resembling the figure eight. U.S. Pat. No. 5,177,826 (Vrignaud et al.) reports a pair of disc-like rotary brushes mounted for rotation about an axis generally perpendicular to a length of the handle. Between the rotary pair are upper and lower linear brushes rotating in a linear reciprocating motion generally perpendicular to the axis. A cylindrical cam element mounted for eccentric rotation operates as part of the system. A further gear is secured to the cam element, but mounted for concentric rotation. U.S. Pat. No. 5,077,855 (Ambasz) describes an electric toothbrush including a drive unit having a motor and a transmission that simultaneously drive a shaft and a brushhead extension reciprocably in a direction parallel to the axis of the shaft. A brush unit includes a brushhead coupled to the extension for lengthwise reciprocating motion on which several bristle holders, each carrying several bristle tufts, are mounted individually for pivotal movement about an axis spaced apart from and parallel to the drive shaft. A crank coupled to the drive shaft imparts pivotable movement to each bristle holder individually.

Even with the options and improvements categorized above, most of the mechanical designs remain complex. Many small parts are required to impart a rotary motion to the bristles or head. Furthermore, the necessarily miniature character of these parts and their unsealed arrangement accelerates wear in the abrasive environment typical of the oral cavity.

Another significant problem is that of efficacy. Electric toothbrushes when compared to the manual variety are not more efficient. For instance, little difference has been seen in their respective tartar removal performance.

Still another major shortcoming of the known art is its non-conformance to best practice toothbrush movement. Most periodontology graduate program textbooks promote the Bass technique. It is recommended for bacterial plaque removal adjacent to and directly beneath the gingival margin. This area is the most significant in the control of gingival and periodontal disease. Elements of the Bass technique include positioning the brush along the gum line at a 45° angle. One row of the bristles should be nestled slightly under the gums where they meet the teeth. Thereafter the brush is gently wiggled back and forth ten times to loosen plaque within the hidden fold along the gum line. In a final step, the brush is lifted away and repositioned to perform the same motion with the next set of teeth and gums.

Accordingly, it is an object of the present invention to provide an electric toothbrush delivering three dimensional motion to the bristles.

It is another object of the present invention to provide an electric toothbrush delivering a three dimensional motion which conforms to the Bass technique for bacterial plaque removal adjacent to and directly beneath the gingival margin.

Still a further object of the present invention is to provide an electric toothbrush of simpler mechanical design and which permits less costly replacement of brushheads than those normally associated with mechanical drive systems presently in commerce.

These and other objects of the present invention will become more readily apparent through the following summary and detailed description.

SUMMARY OF THE INVENTION

An electric toothbrush is provided which includes:

(i) an elongate body defining a handle and having an interior cavity formed therein, the cavity extending from a front to a rear end;

(ii) a power source mounted within the cavity;

(iii) an elongate drive shaft aligned from front to rear end driven rotatably by the power source;

(iv) a camwheel mounted on the drive shaft;

(v) a yoke with projecting arms, the camwheel axially reciprocating between the projecting arms thereby imparting a reciprocating movement to the drive shaft;

(vi) a crankshaft section axially downstream from the yoke and being driven by the drive shaft;

(vii) an output shaft axially aligned with the drive shaft; and (viii) a collar with a guide track eccentrically coupling the crankshaft section to the output shaft thereby imparting both lateral and reciprocating rotary motion to the output shaft.

The mechanical drive system embraces within a closed housing a completely self contained three dimensional system. No mechanical drive aspects are required external to the brush handle housing in order to provide a brushing action.

A simple brushhead is positioned telescopically onto the output shaft. Retention is best achieved by a detent. No moving parts are necessary in the brushhead and it can be formed from a short, hollow shaft.

The combined lateral and reciprocating rotary movement of the output shaft is transmitted to the brushhead. Each individual brush tip fiber of the brushhead is caused to move clockwise in a predicable oval pattern. The fiber tips move in concert to create an overlapping scrubbing pattern. Travel of the brush tips are conducive to improved cleaning of tooth interstices and gum lines in a manner suggested by the Bass technique.

Advantageously the camwheel is canted between 1 and 20° relative to the drive shaft. More preferably the cant ranges from 4 to 10°.

The output shaft downstream from the collar has a flexible section adjacent the front end of the elongate body. Bending can occur along that section at an angle between 1 and 40°.

DETAILED DESCRIPTION OF THE DRAWING

Various features, objectives and benefits of the present invention will become more readily apparent through consideration of the following drawing in which:

FIG. 1 is a side elevational view of an electric toothbrush according to the present invention;

FIG. 2 is the toothbrush according to FIG. 1 with a section of the outer housing removed to reveal the drive mechanism;

DETAILED DESCRIPTION OF THE INVENTION

Figure 3:
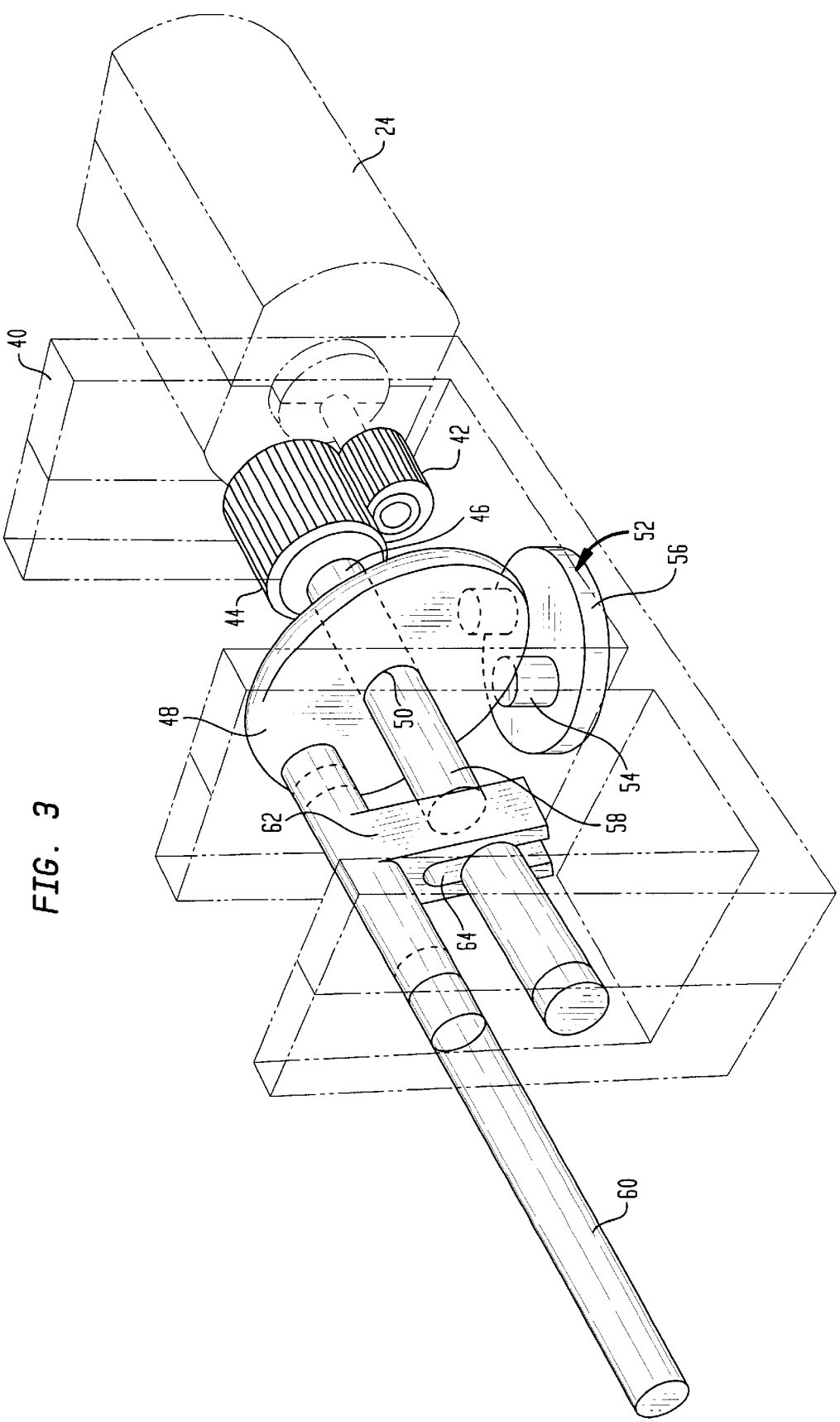
FIG. 3 is an expanded view of a section along the drive mechanism shown in FIG. 2.

FIG. 1 provides a view of the first embodiment of the present invention. The electric toothbrush shown in this figure includes an elongate body 2 defining a handle 4 and an interior cavity 6 formed within the body. The cavity extends from a front end 8 to a rear end 10. A brushhead member 12 is positioned on the front end of the elongate body retained through a detent 14. The brushhead member includes a bristle bundle array 16 projecting from a head 18.

Brushhead member 12 surrounds flexible shaft 20, the latter representing a terminus of the electric toothbrush drive mechanism. Coupling of the flexible shaft to the brushhead member allows for an ergonomically angled head in respect to the handle 4. Water resistant seal 22 surrounds the flexible shaft to protect the electrical mechanism from the external environment. Within cavity 6 towards the rear end is positioned a miniature motor 24. Battery 26 positioned in close proximity to the motor serves as an energy source. An induction charging coil 28 is located at the rear end of the elongated body and electrically connected to an electronic control board 30. The battery is rechargeable by connecting the coil to a standard 120 AC outlet source. Start and stop control buttons 32, 34 are positioned on an external wall of the elongated body directly above the electronic control board. A charging light 36 is stationed at a lower end of the control board as an indicator of battery recharge level.

An understanding of details of the drive mechanism assembly 38 can best be understood by review of FIG. 2 in conjunction with FIG. 1. A more detailed view is found in FIG. 3. Driven gear 42 is positioned adjacent and activated by motor 24. Coupled to the driven gear is a smaller drive gear 44 with a reduction ratio of approximately 2:1 respectively. Other embodiments may utilize reduction gear ratios ranging anywhere from about 10:1 to about 1.2:1. Space considerations place a premium on a minimum number of gears although other embodiments may employ a greater number of reduction gears and in different spatial arrangements.

An elongate drive shaft 46 rotatably communicates from drive gear 44 onto which the latter is force fitted. A camwheel 48 having a central aperture 50 is supported by the drive shaft 46 which force fittingly penetrates the central aperture. Camwheel 48 is positioned at a cant angle of approximately 6°. Bracketing the camwheel is a yoke 52 with arms 54 projecting from a circular mounting base 56. Travel of the camwheel is laterally restricted by placement between the arms of the yoke.

Downstream from the yoke is a crankshaft section 58 driven by the driveshaft 48. Axially aligned (i.e. parallel) with the reciprocating drive shaft 46 is an output shaft 60. Eccentrically coupling the crankshaft section to the output shaft is a collar 62 formed with a guide track 64 through which the crankshaft traverses. Support for the drive mechanism is achieved by a stiff frame 40. Suitable materials for the frame are injection molded plastics such as nylon.

A flexible section 66 of the output shaft downstream from the collar is bent at an angle between 1 and 40°.

Power transmission begins with pressure on the start button activating the battery. Electrical connection causes the motor to rotate transmitting rotational motion via a short shaft to turn the driven gear. The latter couples with the larger drive gear causing rotation in an opposite direction. Since the drive gear is firmly attached to the drive shaft, the camwheel, in turn, rotates. Outer rims of the camwheel rotate in continuous close contact to the projecting arms of the yoke. The base of the yoke freely swivels about its circular axis to accommodate a continuously changing approach angle generated by the camwheel as it rotatingly travels between the yoke arms. A constant fixed contact of the arms is therefore maintained with the rim of the camwheel. As a result, a reciprocating motion of the crankshaft occurs. This motion is then further transmitted to the collar via the crankshaft section spinning eccentrically.

Reciprocating motion of the crankshaft section is thereby transferred directly to the collar and output shaft. Further, it must be noted that the eccentric crankshaft section acting upon the collar imparts an oscillating motion to the output shaft in concert with the reciprocating motion. The combination produces a compound motion of the brushhead as it is turned by its shaft through positive engagement with the flexible section of the output shaft.

Figure 4:
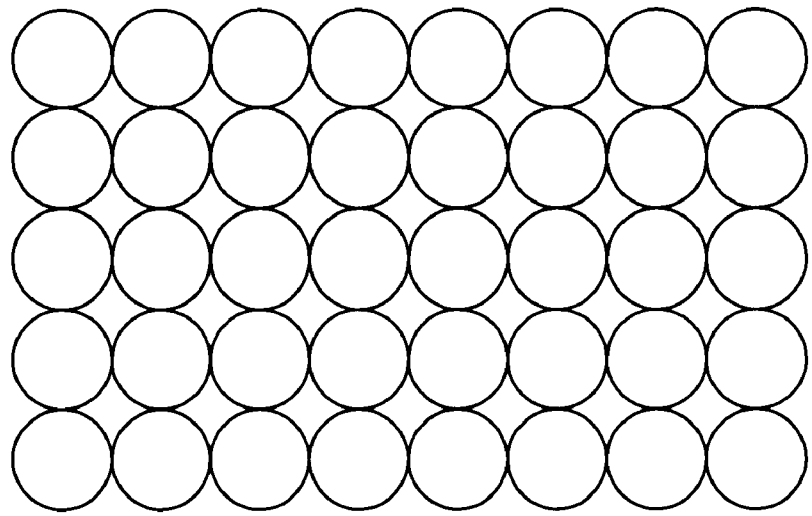
FIG. 4 is a top view of a bristle bundle array.
Figure 5:
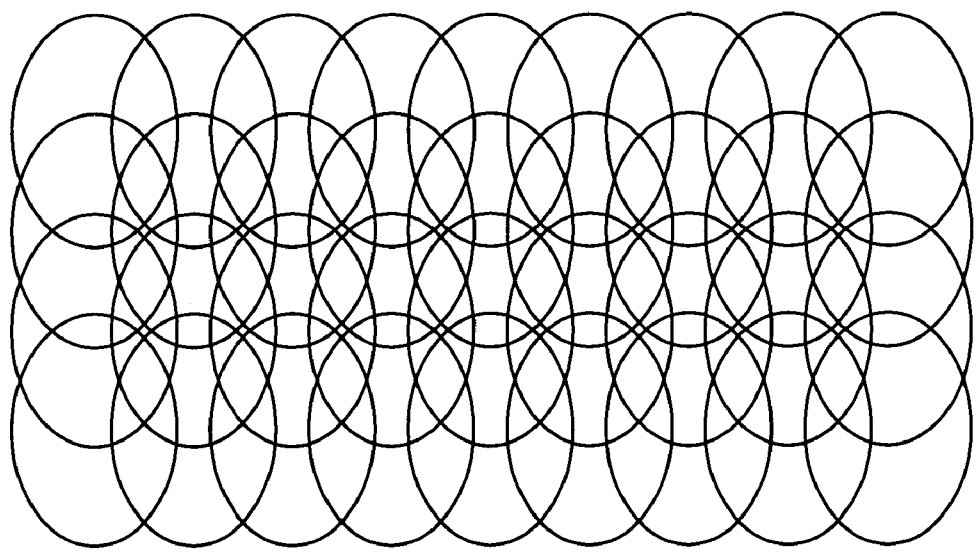
FIG. 5 is a travel pattern generated when the bristle bundle array of FIG. 4 is vibrated by the mechanism shown in FIG. 3.

FIG. 4 displays a top view of the bristle bundle array. Motion of bristles within the array are shown in FIG. 5. Substantially overlapping travel paths are generated by the combination of motion generated through the drive assembly mechanism of this invention. Overlapping travel paths closely match the brushing pattern most recommended by dentists. Travel of the brush bristles occurs at relatively high speed producing a multiplicity of overlapping scrubbing strokes. These cross back and forth over a tooth surface.

It is to be understood that bristle arrays other than those illustrated can be suitable for toothbrushes of this invention.

The bristles may be cut at angles to facilitate proper brushing of teeth which may lie awkward to reach within the oral cavity. The angle may be further adjusted in combination with the brushhead member to closely conform the angle referred to as the Bass angle A by periodontal and dental practitioners.

The foregoing description and examples illustrate selected embodiments of the present invention. In light thereof variations and modifications will be suggested to one skilled in the art, all of which are within the spirit and purview of this invention.

What is claimed is:

1. An electric toothbrush comprising:
   (i) an elongate body defining a handle and having an interior cavity formed therein, the cavity extending from a front to a rear end;
   (ii) a power source mounted within the cavity;
   (iii) an elongate drive shaft aligned from front to rear end driven rotatably by the power source;
   (iv) a camwheel mounted on the drive shaft;
   (v) a yoke with projecting arms, the camwheel axially reciprocating between the projecting arms thereby imparting a reciprocating movement to the drive shaft;
   (vi) a crankshaft section axially downstream from the yoke and being driven by the drive shaft;
   (vii) an output shaft parallel with the drive shaft; and
   (viii) a collar with a guide track eccentrically coupling the crankshaft section to the output shaft thereby imparting both lateral and reciprocating rotary motion to the output shaft.

2. The electric toothbrush according to claim 1 wherein the camwheel has a cant between 1 and 20° relative to the drive shaft.

3. The electric toothbrush according to claim 2 wherein the cant ranges from 4 to 10°.

4. The electric toothbrush according to claim 1 wherein the output shaft downstream from the collar adjacent the front end has a flexible section allowing bending at an angle between 1 and 40°.

5. The electric toothbrush according to claim 1 wherein the yoke has a circular mounting base and is partially rotatable.

6. The electric toothbrush according to claim 1 further comprising a brush head member replaceably removable from a front end of the elongate body and separated therefrom by a rubber seal.

* * * * *